(12) United States Patent
Mosseri

(10) Patent No.: US 6,238,872 B1
(45) Date of Patent: *May 29, 2001

(54) TARGETED THERAPY TO A BIOMEDICAL DEVICE

(75) Inventor: Salomon Mosseri, Paris (FR)

(73) Assignee: S.E.T.-Smart Endolumenal Technologies Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/162,721

(22) Filed: Sep. 30, 1998

Related U.S. Application Data

(63) Continuation-in-part of application No. 08/831,387, filed on Apr. 1, 1997, now Pat. No. 5,925,353.

(51) Int. Cl.$^7$ ................................................. G01N 33/53
(52) U.S. Cl. ................................. 435/7.1; 600/1; 600/3; 600/36; 604/101; 606/194; 623/1; 623/11; 623/12; 424/1.49; 424/423
(58) Field of Search .................. 600/1, 3, 36; 424/1.49, 424/423, 130.1, 178.1; 435/4, 7.1; 604/101; 606/194, 195; 623/1, 11, 12

(56) References Cited

U.S. PATENT DOCUMENTS

| | | | |
|---|---|---|---|
| 5,131,907 | * | 7/1992 | Williams et al. .................... 600/36 |
| 5,554,182 | * | 9/1996 | Dinh et al. ............................ 623/1 |
| 5,607,475 | * | 3/1997 | Cahalan et al. ..................... 623/11 |
| 5,643,712 | | 7/1997 | Brasile . |
| 5,925,353 | * | 7/1999 | Mosseri ........................... 424/178.1 |

OTHER PUBLICATIONS

Bosslet et al, "Generation of Bispecific Monoclonal Antibodies for Two Phase Radioimmunotherapy", *Br. J. Cancer*, 63:681–686, 1881.

Landzberg et al, "Pathophysaiology and Pharacological Approaches for Prevention of Coronary Artery Restenosis Following Coronary Artey Balloon Angioplasty and Related Procedures", *Progreess in Cardiovasculoar Diseases*, 39(4):361–398, 1997.

Kranenborg et al, "Development and Characterization of Anti–Renal Cell Carcinoma X Antichelate Bispecific Monoclonal Antibodies for Two–Phase Targeting of Renal Cell Carcinoma", *Cancer Res.* (Suppl), 55:5864s–5867s, 1995.

Lambert, et al, "Localized Arterial Wall Drug Delivery from a Polymer–Coated Removable Metallic Stent", *Circulation*, 90:1003–1011, 1994.

Van Belle et al, "Stent Endotheliazation", *Circulation*, 95:438–448, 1997.

Yao et al, "Improved Targeting of Radiolabeled Streptavidin in Tumors Predtargeted with Biotinylated Monoclonal Antibodies Through an Avidin Chase", *J. Nucl. Med.*, 36:837–841, 1995.

DeNardo et al, "Pharmacokinetics of Chgimeric L6 Conjugated to Indium–111– and Yttrium–90–DOTA–Peptide in Tumor–Bearing Mice", *J. Nucl. Med*, 36:829–836, 1995.

Thrush et al, "Immunotoxins: An Update", *Ann Rev Immunol*, 14:49–71, 1996.

Wilder et al, Radioimmunotherapy: Recent Results and Future Directions, *J. Clin. Oncology*, 14(4):1383–1400, 1996.

Goodwin et al, "Pretargeting", *Cancer (Suppl)*, 80(12):2675–2680, 1997.

Larson et al, "SingleChain Antigen Binding Protein (sFv CC49)", *Cancer (Suppl)*, 80(12):2458–2468 (1996).

Meares et al, "Macrocyclic Chelates of Radiometals for Dianosis and Therapy", *Br. J. Cancer*, 62(Suppl X):21–26, 1990.

* cited by examiner

*Primary Examiner*—Sheela Huff
(74) *Attorney, Agent, or Firm*—D'vorah Graeser

(57) ABSTRACT

A biomedical device assembly, such as a stent, for the targeted treatment of a tissue, such as the inhibition of restenosis. The stent is coated with an antigen, which is an example of a lock. The antigen can be bound by a labelled antibody, which is an example of a key and an effector. The antibody is preferably labelled with a radioactive source. According to one method of preparing the biomedical device assembly, after the stent has been placed in the blood vessel of the subject, the antibody is injected. The antibody then binds to the antigen on the stent, thereby localizing the radioactive source to the area to be treated, for example for restenosis. Other biomedical devices, such as a coil, an artificial valve or a vascular graft, could also be used in the place of the stent. The biomedical device could be placed in another biological passageway, such as the gastrointestinal tract, an airway or the genitourinary tract.

12 Claims, 8 Drawing Sheets

TARGETED THERAPY TO A BIOMEDICAL DEVICE

This Patent Application is a Continuation in Part of U.S. patent application Ser. No. 08/831,387, filed on Apr. 1, 1997, now U.S. Pat. No. 5,925,353.

FIELD AND BACKGROUND OF THE INVENTION

The present invention relates to the targeting of a therapeutic effector to a biomedical device and, in particular, to the use of radioimmunotherapy for the localization of radioactivity to stents for the reduction or elimination of restenosis.

Restenosis of blood vessels occurs after narrowed or occluded arteries are forcibly dilated by balloon catheters, drills, lasers and the like, in a procedure known as angioplasty. Such forcible dilation is required in order to reopen arteries which have been narrowed or occluded by atherosclerosis. However, up to 45% of all arteries which have been treated by angioplasty return to their narrowed state through the process of restenosis. Restenosis is caused by a number of mechanisms, such as recoil of the vessel wall towards its original dimensions, neointimal hyperplasia induced by trauma to the vessel wall, accumulation of extracellular matrix, remodeling of the tissue and other biological processes. Restenosis can significantly reduce the efficacy of angioplasty and as such is a major barrier to the effective treatment of narrowed arteries.

Attempts to reduce or eliminate restenosis have generally focused on the insertion of biomedical devices, such as stents, within the treated artery. Stents can reduce restenosis by preventing recoil of the treated blood vessel to its original dimensions. Various stents are known in the art, including coils and sleeves, those which are expandable by balloon catheters, heat expandable and self-expandable stents. Unfortunately, stents alone cannot prevent restenosis caused by neointimal hyperplasia of the tissues of the vessel wall. In fact, the stent material itself may accelerate such hyperplasia, since it is foreign to the body tissues.

Recently, as noted above, radionuclear irradiation of blood vessels has been proposed as a method of preventing restenosis caused by neointimal hyperplasia. The application of radionuclear irradiation to the body of a subject is a well accepted mode of therapy in medicine. The main use of such irradiation is for treating both malignant and benign tumors. Radionuclear irradiation can also be used to inhibit the undesired proliferation of cells in other rapidly growing tissues, such as keloids and blood vessels undergoing restenosis.

One study showed that such irradiation completely prevented restenosis of the treated arteries [H. D. Bottcher et al., Int. J. Radiation Oncology Biol. Phys., 29:183–186, 1994]. A number of studies in animal models also support the efficacy of radionuclear irradiation of blood vessels for the prevention or reduction of restenosis following angioplasty [J. G. Wiedermann et al., JACC, 23:1491–8, 1994; R. Waksman et al., Circulation, 92:3025–3031, 1995; R. Waksman et al., Circulation, 91:1533–1539, 1995]. Thus, clearly exposing the walls of blood vessels to radioactivity is a valuable method of preventing and treating restenosis caused by neointimal hyperplasia.

Currently, radionuclear irradiation of blood vessels is performed by the insertion of temporary or permanent radionuclear sources into the vessels. For example, radioactive yttrium-90 wires were inserted into the central lumen of a balloon catheter in order to irradiate blood vessel walls [Y. Popowski et al., Int. J. Radiation Oncology Biol. Phys., 43:211–215, 1995]. Other radioactive sources have included iridium-192, administered by catheter to arteries which had been treated by angioplasty [P. S. Teirstein et al, Circulation, 94:I-210, 1996]. U.S. Pat. No. 5,213,561 discloses a device for inserting a radionuclear source into a blood vessel, in which the source of radioactivity is mounted on a stent, for example.

Unfortunately, the insertion of radionuclear sources directly attached a catheter or stent, in which the catheter or stent is radioactive prior to insertion into the blood vessel, has a number of disadvantages. First, such procedures require a highly specialized clinical setting, which is appropriate both for catheterization procedures and for the handling of radioactivity. Second, these procedures are highly invasive. Third, temporary radioactive sources require repeated invasive treatments. However, temporary as well as permanent sources have the further disadvantage of decaying according to their specific half-life. Thus, current methods for irradiating blood vessels have significant disadvantages.

The concept of specifically targeting tumor cells is a goal of modem radio-oncology. The developing field of radiolabelled immunoglobulin therapy (RIT) employs radionuclide-labeled monoclonal antibodies which recognize tumor-associated antigens, thereby selectively targeting tumor cells. Beta particles, alpha particles and gamma rays emitted from a radiolabelled antibody bound to a tumor cell also kill neighboring cells because these particles can penetrate through several cell diameters. In B-cell lymphoma refractory to chemotherapy, RIT has been associated with a high rate of durable remissions [Kaminki et al., JCO, 14:1974–1981, 1996].

RIT may be effective for cancer treatment because tumor cells have special antigens on their surface, against which antibodies can be raised. Unfortunately, the situation is much more complicated for the prevention and treatment of restenosis. Restenotic tissue is not known to express special antigens, to that antibodies against such tissue would also bind to normal blood vessel walls and would not be sufficiently specific for the tissue to be treated. Thus, targeting antibodies directly to the tissue itself is not possible.

However, the specific targeting of effector moieties to restenotic tissue would have many benefits for the treatment and prevention of restenosis. For example, a targeted drug or an isotope could be injected into the patient at a site distant from the catheterized blood vessel. The targeted drug or isotope would remain in the area of catheterization, specifically treating the restenotic tissue without serious or problematic side effects. Furthermore, the targeted effector could be injected substantially after catheterization, which would permit the effector to be injected at a different location. For example, if the effector was an isotope, the injection could be performed in a special facility for treatment with radioactivity. In addition, the effector could potentially be selected according to the degree of severity of restenosis, which could be monitored after the insertion of the catheter or stent. Thus, the separation of the procedures for catheterization and for treatment with an effector would clearly increase the flexibility of treatment for restenosis.

Of course, restenosis is not the only pathological condition which could benefit from treatment with a targeted effector. Other types of biomedical devices can cause pathological overgrowth or ingrowth of tissue surrounding the insertion point of the device. Such pathological tissue growth in the area of an inserted biomedical device can be difficult to treat, as these devices are not always immediately accessible through surgery, for example. Treatment with a targeted effector, which would be specifically localized to the tissue surrounding the biomedical device without the requirement for additional surgery, would clearly be highly beneficial. Moreover, such a device may be purposefully implanted into a tumor in order to provide highly localized treatment of malignancies, particularly for solid tumors.

There is thus a widely recognized need for, and it would be highly advantageous to have, a method of targeting an effector, such as a radioactive isotope, to specific areas near an inserted biomedical device, such as a blood vessel, in order to perform localized therapy for the treatment or prevention of a pathological condition, such as restenosis of a catheterized blood vessel.

SUMMARY OF THE INVENTION

It is one object of the present invention to provide localized therapy to a tissue or to a biological passageway.

It is another object of the present invention to provide such localized therapy by targeting an effector to a biomedical device, such that the area surrounding the biomedical device is treated.

It is still another object of the present invention to target the effector to the biomedical device with a lock and key system, in which the key is attached to the effector and the lock is attached to the biomedical device.

It is yet another object of the present invention to provide a method for manufacturing such a biomedical device.

These and other objects of the present invention will become apparent from the following description, claims and figures.

According to the teachings of the present invention, there is provided a biomedical device assembly comprising a biomedical device, wherein the biomedical device features an antigen and an antibody having a label attached, wherein the antigen and the antibody are bound. Preferably, the biological passageway is selected from the group consisting of blood vessel, airway, gastrointestinal tract, intracerebral, bile duct and genitourinary tract. More preferably, the biological passageway is a blood vessel.

Preferably, the antigen is a drug molecule. Also preferably, the biomedical device is selected from the group consisting of coil, artificial valve, vascular graft and stent. More preferably, the biomedical device is a stent.

Preferably, the label is selected from the group consisting of radioactive source and pharmaceutical moiety. More preferably, the label is a radioactive source.

According to another embodiment of the present invention, there is provided a method of substantially inhibiting restenosis in a blood vessel of a subject, comprising the steps of: (a) inserting a stent into the blood vessel of the subject, the stent having an antigen attached; and (b) administering an antibody to the subject, the antibody being capable of binding to the antigen and the antibody having a label attached wherein the label is capable of inhibiting restenosis.

Preferably, the label is selected from the group consisting of radioactive source and pharmaceutical moiety. More preferably, the label is a radioactive source. Preferably, the antigen includes a plurality of different types of antigens, such that the step of administering the antibody is repeated for a plurality of different types of antibodies.

According to another embodiment of the present invention, there is provided a biomedical device assembly for targeted treatment, comprising: (a) a biomedical device; (b) a lock, the lock being attached to the biomedical device; (c) a key for specifically interacting with the lock; and (d) an effector for performing the targeted treatment, the effector being attached to the key.

Preferably, the key and the lock are each individually selected from the group consisting of an antibody, an antigen, a non-regular antibody, a mixed proteinaceous and non-proteinaceous combination, and a non-proteinaceous molecule, and combinations thereof. More preferably, the antibody is selected from the group consisting of a polyclonal immunoglobulin, a monoclonal immunoglobulin, a SFv (single chain antigen binding protein), $Fab^1$ fragment, a $Fab^2$ fragment and a humanized monoclonal immunoglobulin.

Also more preferably, the antigen is selected from the group consisting of a protein, a peptide and fragments thereof, a carbohydrate macromolecule, an oligonucleotide and a pharmaceutical molecule, and combinations thereof. Most preferably, the protein is selected from the group consisting of avidin and biotin.

According to preferred embodiments of the present invention, the non-regular antibody is selected from the group consisting of a macromolecule of IgG, a bifunctional antibody, avidin and biotin. Preferably, the non-proteinaceous molecule is selected from the group consisting of a carbohydrate macromolecule, an oligonucleotide and a bifunctional chelator. Also preferably, the mixed proteinaceous and non-proteinaceous combination is a protein with an attached oligonucleotide.

According to other preferred embodiments of the present invention, the effector is selected from the group consisting of a radioactive isotope, a drug, a hormone, a growth factor, a cytokine, a T-cell, a toxin, an endothelial cell, a chelate of a radioactive isotope and a bi-component effector. Preferably, the chelate of the radioactive isotope includes a chelator selected from the group consisting of DOTA, DTPA, nitro-benzyl DOTA and a bifunctional chelator. More preferably, the radioactive isotope is selected from the group consisting of yttrium 90 ($^{90}Y$), lutetium 177 ($^{117}Lu$), rhenium 186 ($^{186}Re$), rhenium 188 ($^{188}Re$), bismuth 212 ($^{212}Bi$), astatine 211 ($^{211}At$), iodine 131 ($^{131}I$), iodine 125 ($^{125}I$) and copper 67 ($^{67}Cu$). Preferably, the bi-component effector is an enzyme and a prodrug, wherein the enzyme chemically alters the prodrug to activate the prodrug. Also preferably, the toxin is selected from the group consisting of a plant toxin, a bacterial toxin, a fungal toxin and a synthetic toxin.

According to still other preferred embodiments of the present invention, the lock is attached to a material coating at least a portion of a surface of the biomedical device. Preferably, the material is selected from the group consisting of a derivatizable polymer and a metal. More preferably, the material is the derivatizable polymer and the lock is attached to the derivatizable polymer by a covalent bond. Most preferably, the covalent bond is formed by a chemical reaction between the lock and the derivatizable polymer. Also most preferably, the chemical reaction is activated by exposure of the lock and the derivatizable polymer to ultraviolet light.

Preferably the lock is attached to the derivatizable polymer by a noncovalent bond.

According to yet another embodiment of the present invention, there is provided a method for manufacturing a biomedical device assembly, the method comprising the steps of: (a) providing a biomedical device; (b) attaching a lock to the biomedical device; (c) attaching an effector to a key to form an attached effector; and (d) incubating the lock and the key, such that the lock and the key interact to form the biomedical device assembly.

Preferably, the step of attaching the lock to the biomedical device is performed ex vivo, and the step of incubating the lock and the key to form the biomedical device assembly is performed by first placing the biomedical device with the lock in a subject, and then administering the key with the attached effector to the subject, such that the biomedical device assembly is formed by an interaction of the key and the lock in the subject. Alternatively, and preferably, the step of attaching the lock to the biomedical device is performed ex vivo, and the step of incubating the lock and the key to form the biomedical device assembly is performed ex vivo.

Hereinafter, the terms "radionuclide" and "radioactive isotope" include, but are not limited to, yttrium 90 ($^{90}$Y), lutetium 177 ($^{177}$Lu), rhenium 186 ($^{186}$Re), rhenium 188 ($^{188}$Re), phosphorous 32 ($^{32}$P), bismuth 212 ($^{212}$Bi), astatine 211 ($^{211}$At), iodine 131 ($^{131}$I), iodine 125 ($^{125}$I), iridium 192 ($^{192}$Ir), palladium ($^{103}$Pd) and copper 67 ($^{67}$Cu).

Hereinafter, the term "DTPA" includes 1,4,7-triazaheptane-N,N',N"-pentaacetic acid) and derivatives thereof. The term "DOTA" includes 1,4,7,10-tetraazacyclododecane-N,N',N",N"'-tetraacetic acid and derivatives thereof.

Hereinafter, the terms "Sfv" and "single chain antigen binding protein" refer to a type of a fragment of an immunoglobulin, an example of which is sFv CC49 (Larson, S. M. et al., Cancer, 80:2458–68, 1997).

BRIEF DESCRIPTION OF THE DRAWINGS

The invention is herein described, by way of example only, with reference to the accompanying drawings, wherein.

BRIEF DESCRIPTION OF THE INVENTION

Figure 1:
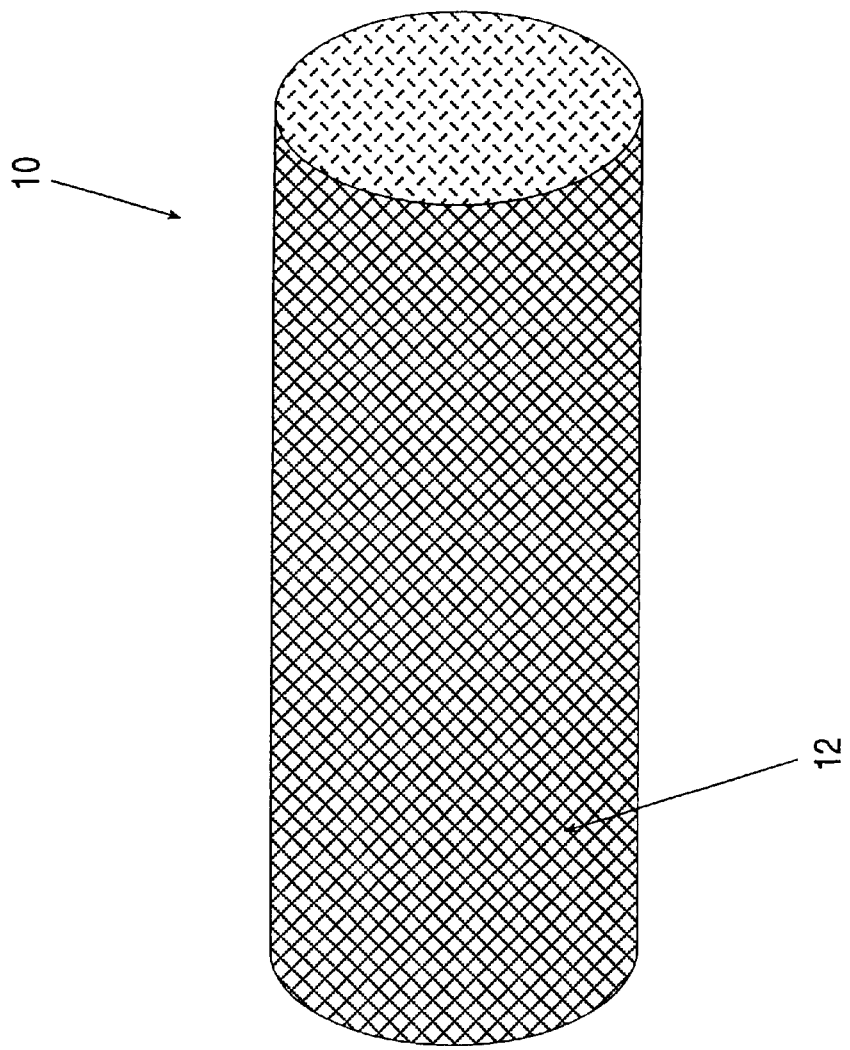
FIG. 1 is a schematic illustration of an exemplary biomedical device according to the present invention.

The present invention is directed towards a method and a device for the targeted treatment of a tissue with an effector. The effector is targeted to the tissue to be treated by a "lock and key" system. The "lock and key" system includes a "lock" attached to a biomedical device, which is inserted into a subject as part of a regular insertion procedure. The "key" is attached to an effector. In some circumstances, the "key" and the effector may be the same molecule or complex. The effector/key combination is then injected into the subject, or is otherwise introduced into the subject, at a site which may be at any suitable distance from the point of insertion of the biomedical device. The key enables the effector/key combination to be localized to the biomedical device, by interaction of the key and the lock on the biomedical device. For example, the key could bind to the lock, or the lock could bind to the key, or the key and the lock could become mutually bound. Thus, the effector is specifically targeted to the tissue surrounding the biomedical device.

Examples of suitable combinations of lock and key systems include, but are not limited to, an antibody and antigen combination, non-immunological proteins such as avidin and biotin, and non-protein macromolecules such as complex carbohydrate ligands and receptors. These systems could be adapted from known lock and key systems, such as antibody and antigen combinations. Alternatively, non-protein macromolecules, such as carbohydrates or oligonucleotides, could be specifically designed and synthesized to interact as ligands and receptors. Such non-protein macromolecules would have a number of advantages, including reduced degradation by the body and reduced likelihood of undesirable cross-reactions with other tissues in the body. Thus, many different lock and key systems could be used to target effectors to biomedical devices.

The designation of one component of the system as a "lock" and another component as a "key" is also flexible. For example, an antibody could be an example of a key, while the corresponding antigen would be the lock. In such a situation, the antigen would be attached to the biomedical device and the effector would be attached to the antibody. The antibody/effector combination could then be injected into the patient, for example. Alternatively, the antigen could be the key and the antibody could be the lock. The antibody would be attached to the biomedical device and the effector would be attached to the antigen. Thus, the term "lock" refers to the moiety attached to the biomedical device, while the term "key" refers to the moiety which is either attached to the effector or which is itself an effector, it being understood that the same molecule could be either a lock or a key.

As another preferred embodiment, the bond between the key and the lock is preferably designed to disintegrate or degrade after a certain period of time has elapsed, for example through the dissociation constant of the antigenantibody complex, or alternatively for example through autoradio lysis. Autoradio lysis is the destruction of the protein to which the radio-isotope is attached by the radio-isotope itself.

The term "effector" includes any molecule, combination of molecules or even a complete cell, which has a therapeutic effect. For example, the effector could be a radioactive isotope, a drug, a hormone, a growth factor, a cytokine, a T-cell or a toxin. The effector could be selected in order to inhibit tissue growth, for example to treat or prevent restenosis. Another example of an effector could be an endothelial cell, particularly for coating the interior surface of a stent in order to prevent formation of thrombi and to enable treatment of the surrounding tissue with endothelial cell products such as nitric oxide. In some circumstances, the effector and the key could be the same moiety. For example, a chelate of a metal could specifically bind to a lock, such as an antibody, on a biomedical device. The chelate could include DOTA or DTPA as the chelator, and yttrium or cobalt as the radioactive isotope, for example. Yttrium and cobalt are examples of potentially radioactive isotopes which are used for the inhibition of tissue growth. Thus, many different types of effectors are possible and could be selected by one of ordinary skill in the art.

In addition to the therapeutic uses described previously, these lock and key systems could be used for the manufacture of standard biomedical devices. For example, currently stents are often manufactured with a radioactive isotope already attached to the material of the stent. Such an attached radioactive isotope can then immediately act to prevent restenosis in a catheterized blood vessel. Unfortunately, the ex vivo attachment of a radioactive isotope to the stent at the place of manufacture is potentially problematic. As soon as the radioactive isotope is attached to the stent, the stent must be handled according to the strict regulations for all radioactive material. For example, shipping such radioactive stents is far more complicated than shipping the corresponding non-radioactive stent. The radioactivity is not actually required until just prior to insertion of the stent, however. A far simpler and less complicated manufacturing process would enable the stent and the radioactive isotope to be combined shortly before the stent was inserted into the patient. Thus, the stent and isotope would preferably be manufactured and shipped separately, and then combined at, or just prior to, the time of insertion.

Alternatively, even following current manufacturing processes, the manufacturer could combine the stent and isotope at the point of manufacture of the stent. Such a method would still have an advantage over prior art methods, which require a cyclotron to bombard the stent in order to make the material of the stent radioactive. Thus, the present invention provides for greater flexibility in the manufacture of biomedical devices such as radioactive stents.

The lock and key system described above would also enable the stent and the radioactive isotope to be combined just before insertion. The lock would still be attached to the stent, for example as part of the regular manufacturing process for the stent. The key would still have the radioactive isotope effector attached as part of a key/effector combination. However, the key and effector combination would now be contacted with the lock ex vivo. Once the radioactive material was attached to the stent through the lock and key system, the stent would be inserted into the patient during a regular surgical procedure. Thus, the stent would only become radioactive shortly before insertion into the patient.

The lock and key system of the present invention clearly enables the targeting of an effector to the tissue to be treated, regardless of whether the lock and key are combined in vivo, for example by injection of an antibody with an attached radioactive isotope into a patient, or ex vivo, for example by the attachment of a radioactive isotope to a stent just prior to insertion into the blood vessel of the patient. Thus, the method and device of the present invention clearly enable the targeting of a therapeutic effector to a biomedical device.

DESCRIPTION OF THE PREFERRED EMBODIMENTS

The present invention is directed towards a method and a device for the targeted treatment of a tissue with an effector. The effector is targeted to the tissue to be treated by a lock and key system, in which the lock is attached to a biomedical device, and the key is attached to the effector. For example, the present invention could be used to localize radioactive isotopes to a stent.

The principles and operation of such targeted therapy according to the present invention may be better understood with reference to the drawings and the accompanying description. The following description is specifically directed toward targeted therapy for a stent only as an example, it being understood that many other biomedical devices could also be used. For example, artificial valves, coils or vascular grafts, or other implantable foreign bodies could also be used with the present invention.

EXAMPLE 1

Radioimmunotherapy for a Stent

Referring now to the drawings, FIG. 1 shows an intraluminal stent 10 after deployment within a blood vessel (not shown). Stent 10 can be self-expandable, or inflated with a balloon catheter, for example. Stent 10 can be used for supporting collapsing vessel walls or for expanding partially occluded segments of a dilated blood vessel, catheter-created communication between portal and hepatic veins, narrowed esophagus, intestine, ureters, urethra, intracerebally, bile ducts, or any other duct or passageway in the human body, either in-born, built-in or artificially made.

Stent 10 is preferably and optionally coated with a biocompatible material 12, such that biocompatible material 12 is attached to at least a portion of the surface of stent 10. Hereinafter, the term "attached" includes connected to, or integrally formed with. Biocompatible material 12 can be any material, such as Teflon or Dacron, which is suitable for insertion into the body of a subject. Such materials are well known in the art and could be selected by one of ordinary skill in the art. Alternatively and preferably, stent 10 could be directly formed from a suitable material without the addition of biocompatible material 12. Hereinafter, the term "subject" refers to a human or other mammal on whom the method of the present invention is practiced.

Figure 2:
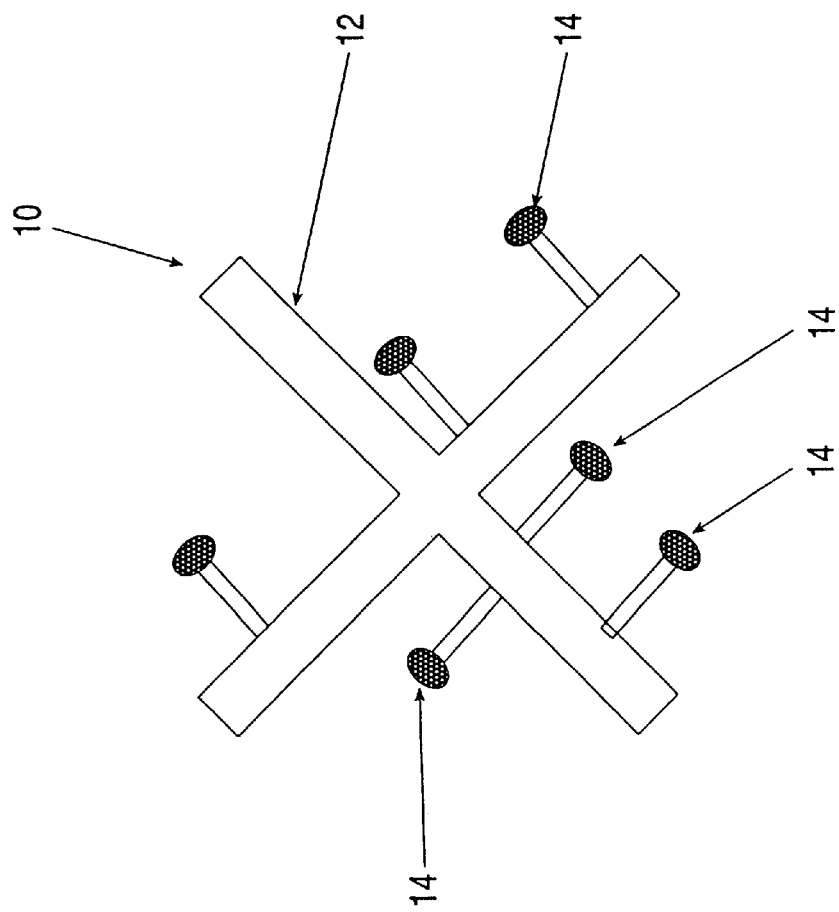
FIG. 2 is a schematic illustration of a portion of the biomedical device of FIG. 1.

FIG. 2 shows a schematic magnification of a portion of the biocompatible material of FIG. 1. Biocompatible material 12 has at least one antigen 14 attached. As noted above, antigen 14 can be any molecule which is bindable by a second molecule, which can be an antibody, for example (not shown). Antigen 14 is one example of a lock of the present invention. Antigen 14 should not be a compound which is present at high levels within the body, or which is accessible to the antibody, since this would reduce localization of the antibody to stent 10 (see below). Accessability could be restricted by using a compound or molecule which is not presented on an extracellular surface, for example. Antigen 14 could be a pharmaceutical molecule such as an antibiotic, digoxin, colchicine and tricyclic antidepressants, for example. The advantage of using a known, clinically tested pharmaceutical molecule is that the safety of such a molecule will already have been extensively tested. Thus, the presence of such a molecule within the body of a subject would not be toxic in and of itself.

Antigen 14 could be either proteinaceous, such as a peptide, a protein or a fragment thereof, or non-proteinacous, such as a pharmaceutical molecule, an oligonucleotide or a carbohydrate macromolecule. The advantage of non-proteinaceous molecules is that they are less likely to be degraded by the body of the subject, and are also less likely to undergo an undesirable cross-reaction with other tissues or molecules of the body of the subject, such as the components of the immune system. Preferably, these molecules would not have any harmful effect on the blood vessel wall itself, although they could act to inhibit restenosis. Most preferably, these molecules would not have been administered to the subject during the implantation of stent 10, or for a suitable time period before and after the implantation of stent 10. Such a suitable time period could be five half-lives of the drug, or any other time period sufficient for the drug to be substantially cleared from the body.

Preferably, antigen 14 is attached to biocompatible material 12 by a chemical reaction. For example, antigen 14 could be attached to biocompatible material 12 by co-incubation with a cross-linking reagent. Most preferably, such a chemical reaction would cause antigen 14 to be presented to the blood vessel for maximum recognition and binding by an antibody (not shown). Alternatively and preferably, antigen 14 could be directly attached to stent 10.

Figures 2, 3:
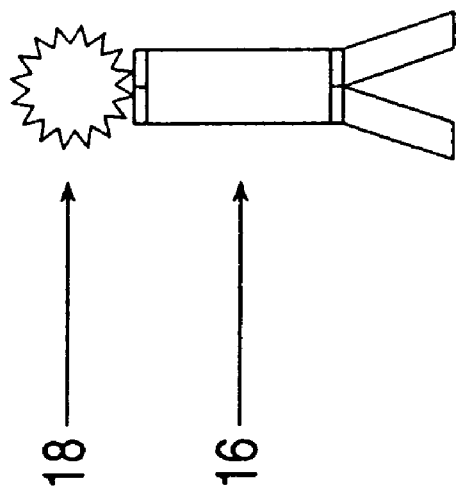
FIG. 3 is a schematic illustration of a portion of an antibody according to the present invention.
Figures 1, 3:
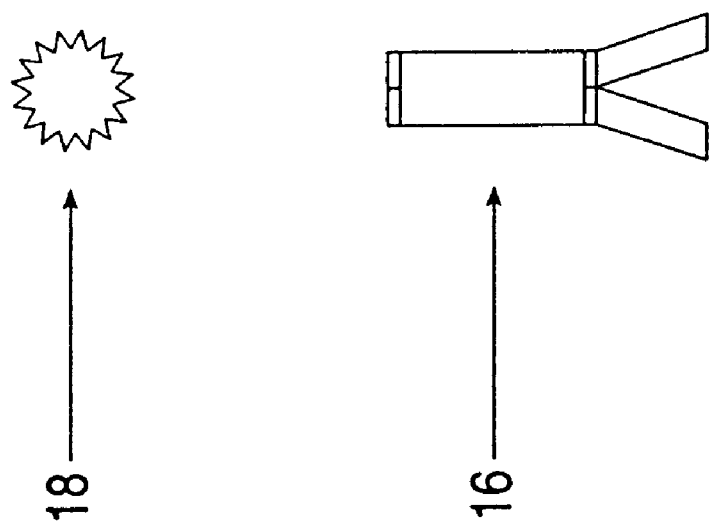

FIG. 3 is an illustration of a labelled antibody. An antibody 16 is shown, with a label 18 attached, and is designated as a "labelled antibody". The term "antibody" hereinafter includes any monoclonal or polyclonal immunoglobulin such as an IgG, or a fragment of an immunoglobin such as sFv (single chain antigen binding protein), $Fab^1$ or $Fab^2$. Antibody 16 could also be a "humanized" monoclonal antibody, in which murine variable regions are fused to human constant regions, or in which murine complementaritydetermining regions are grafted onto a human antibody structure (Wilder, R. B. et al., *J. Clin. Oncol.*, 14:1383–1400, 1996). Unlike mouse monoclonal antibodies, "humanized" monoclonal antibodies often do not undergo an undesirable reaction with the immune system of the subject. Antibody 16 is an example of a key while label 18 is an example of an effector of the present invention.

Label 18 is preferably a radioactive source, which can be any suitable element for medicinal or therapeutic use which emits radioactivity, such as yttrium-90, iodine-132 or iridium-192, for example, and could be selected by someone of ordinary skill in the art. Label 18 could also, alternatively and preferably, be a pharmaceutical moiety, which is a composition used for medicinal or therapeutic purposes, such as an antibiotic, a chemotherapeutic agent, an enzyme, a growth factor, an inhibitor of an enzyme or an inhibitor of a growth factor, for example. Such a pharmaceutical moiety could be in the form of a slow-release formulation, for example. Such pharmaceutical moieties could easily be prepared by one of ordinary skill in the art. Label 18 is an example of an effector according to the present invention, and so could also be selected from those described in any of the Examples or the "Brief Description of the Invention", for example.

The advantage of using a drug molecule for antigen 14 is that antibodies to many of these drugs are commercially available. Of course, new antibodies could be developed according to well known procedures in the art, if required.

Figure 4:
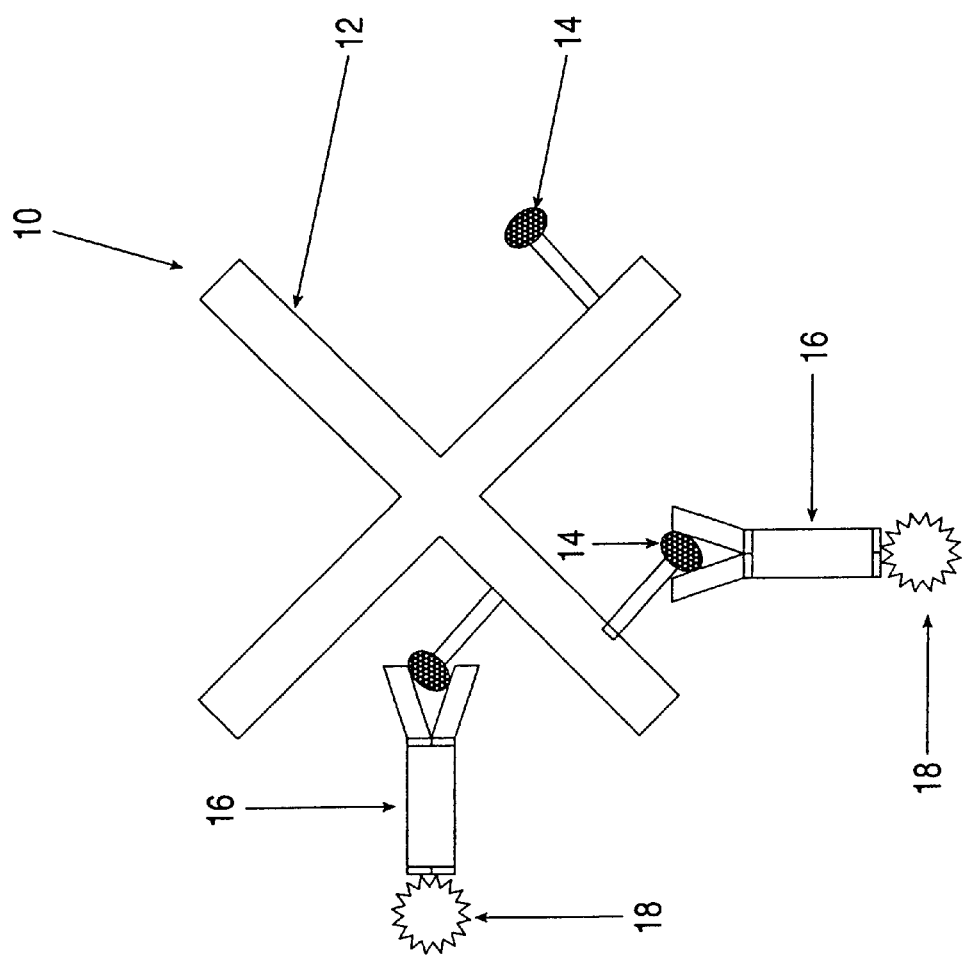
FIG. 4 is a schematic representation of the biomedical device of FIG. 1 with the antibody of FIG. 3.

FIG. 4 is an illustration of the stent after administration of the labelled antibody. Stent 10 has been placed in the blood vessel of a subject, as described for FIG. 1. Antibody 16 has been administered to the subject and is now bound to antigen 14 on biocompatible material 12. The combination of stent 10, antibody 16, antigen 14 and label 18 is an example of a "biomedical device assembly" according to the present invention.

Antibody 16 is preferably administered parenterally, by intravenous injection for example, which is particularly preferable for administration to the genitourinary tract and to blood vessels, for example. Other examples of methods of administration include inhalation into an airway of the subject and oral administration to the gastrointestinal tract, for example. Since antibody 16 is labelled with label 18, the tissue of the blood vessel wall is now being specifically treated. For example, if label 18 is a radioactive source, the tissue is now being specifically irradiated. However, since antigen 14 is substantially only present on stent 10, substantially only the tissue of that portion of the blood vessel wall which is to be treated is being irradiated, in the case of a radioactive source for label 18. Thus, restenosis of the blood vessel is specifically inhibited, without exposing large areas of the body of a subject to radioactivity. Such specific inhibition could be used either for prevention or treatment, or both, of restenosis.

Furthermore, since stent 10 itself is not directly labelled, stent 10 can be implanted in the blood vessel of a subject according to any suitable catheterization procedure, which is well known in the art. Labelled antibody 16 can then be administered to the subject, at a later time and in a different location, if desired. Thus, stent 10 could be implanted in a standard catheterization laboratory, while antibody 16 could be administered in a standard radionuclear medicine laboratory, if label 18 is a radioactive isotope, for example. Also, catheterization time would not have to be prolonged in order to expose the blood vessels to the radioactive source, and the stents themselves would not require special handling.

Preferably, biocompatible material 12 has more than one type of antigen 14 attached, so that the treatment could be repeated more than once with different antibodies 16. Alternatively and preferably, different labels 18 could also be used in this embodiment, particularly for radioactive sources. The advantage of multiple treatments for such sources is that smaller, and therefore less toxic, amounts of radioactivity could be administered with each treatment. Furthermore, radioactive sources with different penetrating strengths could be used, allowing the sources to be tailored to the biological characteristics of the tissue to be treated. Preferably, antibody 16 could have one or more antigens attached (not shown) to which a second antibody could bind, either at substantially the same time or at a later time of administration. Such an arrangement would also facilitate multiple radioactive sources, or eve n a combination of one or more radioactive sources with another pharmaceutical moiety.

Thus, one example for using this embodiment of the biomedical device assembly would be to first insert stent 10 into a blood vessel of a subject, stent 10 having antigen 14 attached. Next, antibody 16 with label 18 could be administered to the subject. Such a method could be used for inhibiting restenosis in a subject. The term "inhibition" can include both prevention, substantially before restenosis has occurred, or treatment, substantially after restenosis has occurred, or both.

An additional example of a method of use could include the additional step of displacing antibody 16 with attached label 18 by injecting a large amount of antibody 16 without attached label 18, preferably after the period of time required for treatment of the subject has elapsed. This step would cause the displacement of the radioactive complex of antibody 16 with attached label 18, and hence at least a reduction in, and preferably a substantial elimination of, the amount of radioactivity bound to stent 10 by binding to antigen 14 on biocompatible material 12. Such displacement could be usefuil to moderate the an excessive amount of radioactivity bound to stent 10, or to terminate the treatment of the subject to prevent possible side effects of excessive or insufficient radioactivity, for example . Untoward side effects are caused when the amount of radioactivity is outside the therapeutic window, such that an excessive amount of radioactivity may cause fibrosis and an insufficient amount of radioactivity may cause cell proliferation.

EXAMPLE 2

Non-regular Protein Antibody/Antigen Combinations

The term "non-regular protein antibody/antigen combination" is used herein to describe a combination of a protein having antibody-like properties with an antigen, proteinaceous or otherwise. The protein with antibody-like properties is specifically not an immunoglobin such as an IgG, or a fragment of an immunoglobin such as SFv (single chain antigen binding protein), $Fab^1$ or $Fab^2$. Examples of proteins with antibody-like properties include avidin or biotin, a macromolecule of an IgG and a bifunctional antibody, although of course many other examples of such proteins are possible. A suitable effector could be selected from those described in any of the Examples or the "Brief Description of the Invention", for example.

Figure 5:
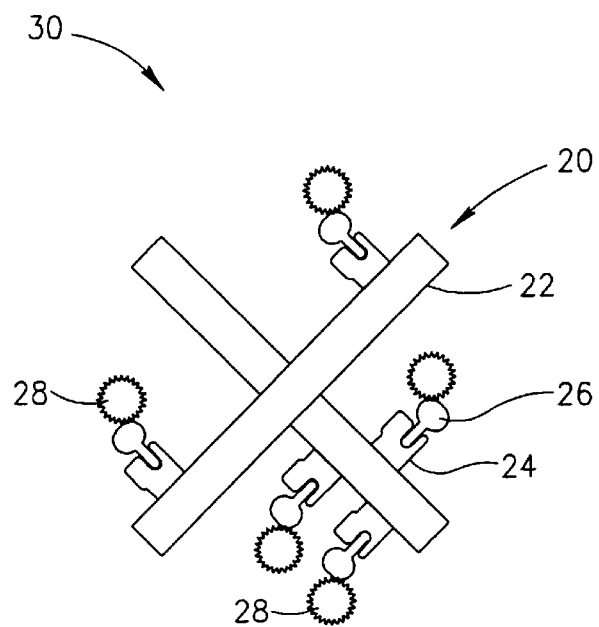
FIG. 5 is a schematic representation of an exemplary biomedical device system according to the present invention with avidin and biotin as the lock and key.

FIG. 5 is an illustration of a biomedical device after administration of a key/effector combination to a subject, in which the key and lock are avidin and biotin. A biomedical device 20, here a stent for the purposes of illustration, has been placed in the subject. Since biomedical device 20 is shown herein as a stent, biomedical device 20 is placed into the blood vessel of the subject. Biomedical device 20 features a biocompatible material 22 to which a lock 24 is attached. Alternatively and preferably, lock 24 is attached directly to biomedical device 20. In this example, lock 24 is either avidin or biotin. Preferably, lock 24 is avidin.

A key 26 with an attached effector 28 has been administered to the subject. Key 26 is now bound to lock 24 on biocompatible material 22. For this example, key 26 is either biotin or avidin. Preferably, key 26 is biotin and lock 24 is avidin. Avidin and biotin are two proteins which are well known in the art to have a high affinity for each other. Therefore, if lock 24 is avidin, biocompatible material 22, or else biomedical device 20, would have avidin proteins attached. If key 26 is biotin, effector 28 would be attached to the biotin protein and then injected into the subject, similarly to the injection of the antibody in Example 1 above. The biotin protein would then specifically bind to the avidin protein, so that lock 24 and key 26 would be bound as shown in FIG. 5. The combination of biomedical device 20, lock 24, key 26 and effector 28 is another example of a biomedical device assembly 30.

Since key 26 is either biotin or avidin, both of which are proteins, the combination of key 26 and effector 28 is preferably administered parenterally, by intravenous injection for example, which is particularly preferable for administration to the genitourinary tract and to blood vessels. Other examples of methods of administration include inhalation into an airway of the subject and oral administration to the gastrointestinal tract, for example.

Once key 26 has bound to lock 24, the tissue surrounding biomedical device 20 is being specifically treated with effector 28. For example, if biomedical device 20 is a stent, the tissue of the blood vessel wall is now being specifically treated. However, since lock 24 is substantially only present on biomedical device 20, substantially only the tissue of that portion of the blood vessel wall which is to be treated is being irradiated, in the case of a radioactive source for effector 28. Thus, if biomedical device 20 is a stent, restenosis of the blood vessel is specifically inhibited, without exposing large areas of the body of a subject to radioactivity. Such specific inhibition could be used either for prevention or treatment, or both, of restenosis.

Furthermore, if effector 28 is a therapeutic substance which could be toxic to those medical personnel handling the substance, such as a radioactive isotope, biomedical device assembly 30 has another advantage. Since biomedical device 20 itself is not directly labelled, biomedical device 20 can be placed within the subject according to any suitable procedure. For example, as a stent, biomedical device 20 could be implanted in the blood vessel of a subject according to any suitable catheterization procedure, which is well known in the art. Key 26 with effector 28 can then be administered to the subject, at a later time and in a different location, if desired. Thus, as a stent, biomedical device 20 could be implanted in a standard catheterization laboratory, while key 26 could be administered in a standard radionuclear medicine laboratory, if effector 28 is a radioactive source, for example. Also, catheterization time would not have to be prolonged in order to expose the blood vessels to the radioactive source, and the stents themselves would not require special handling.

Preferably, biocompatible material 22 has more than one type of lock 24 attached, so that the treatment could be repeated more than once with different keys 26. For example, a first type of lock 24 could be avidin, while a second type of lock 24 could be an antigen as described in Example 1. Alternatively and preferably, different effectors 28 could also be used in this embodiment, particularly for radioactive nuclides. The advantage of multiple treatments for such sources is that smaller, and therefore less toxic, amounts of radioactivity could be administered with each treatment. Another advantage is that cells are more vulnerable at certain points in the cell cycle, such as during mitosis. Multiple treatments are more likely to affect more cells which may be at different points in the cell cycle. Furthermore, radioactive nuclides with different penetrating strengths could be used, allowing the sources to be tailored to the biological characteristics of the tissue to be treated.

Figure 6:
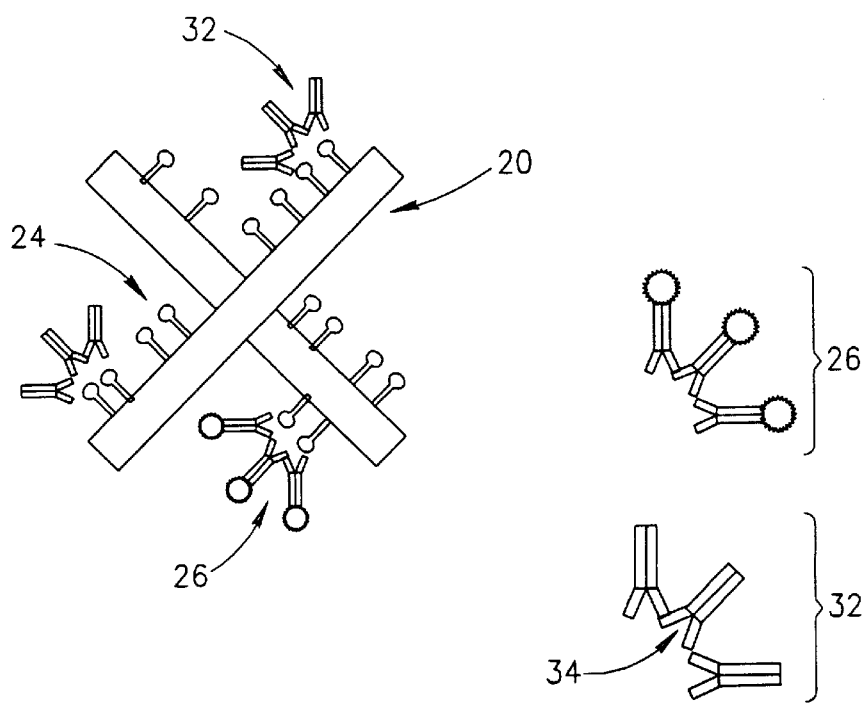
FIG. 6 is a schematic representation of an exemplary biomedical device system according to the present invention with a macromolecule of IgG and an antigen as the lock and key.

FIG. 6 is an illustration of a second type of biomedical device after administration of the key/effector combination to the subject, in which key 26 is a macromolecule of an IgG, and lock 24 is any suitable antigen as described in Example 1 or FIG. 5, for example. As shown in FIG. 6, macromolecule of IgG 32 contains a plurality of antigen-binding sites 34 and is a synthetic molecule. Typically, all of antigen-binding sites 34 bind to the same antigen, which is lock 24. The advantage of macromolecule of IgG 32 over a regular immunoglobulin is that a single macromolecule of IgG 32 can bind to many antigens, which would provide for particularly tight, specific binding. Furthermore, the situation could be reversed, and lock 24 could be macromolecule of IgG 32. Under these circumstances, macromolecule of IgG 32 could bind many keys 26, or antigens, which could be injected into the subject, for example. Thus, as lock 24, macromolecule of IgG 32 could act to concentrate many keys 26 at biomedical device 20.

Figure 7:
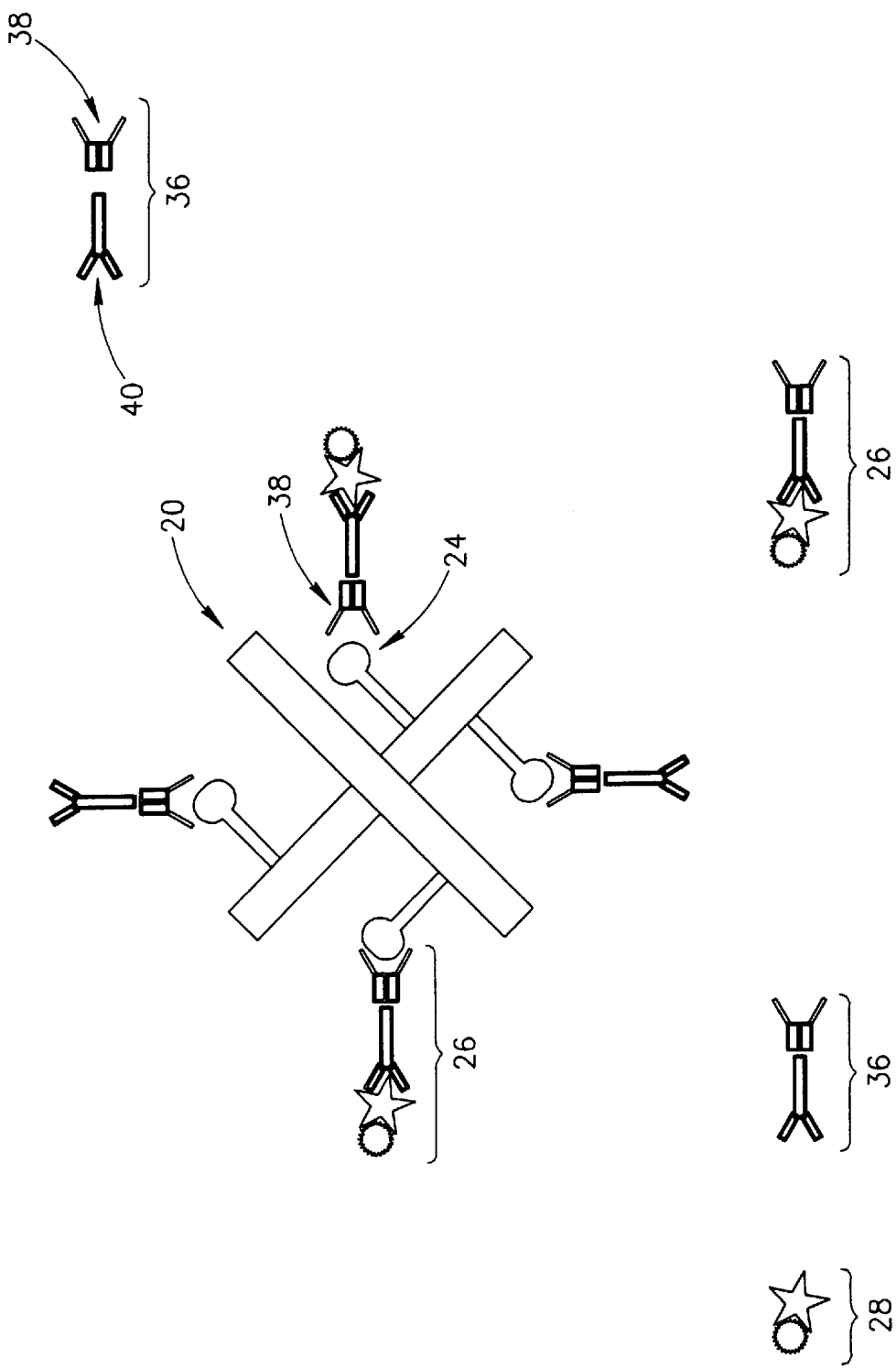
FIG. 7 is a schematic illustration of an exemplary biomedical device system according to the present invention with a bifunctional antibody and an antigen as the lock and key.

FIG. 7 shows yet another embodiment of biomedical device 20, in which key 26 is a bifunctional antibody 36 and lock 24 is any suitable antigen, as described in Example 1 and FIG. 5, for example. Bifunctional antibody 36 has two binding sites. A first binding site 38 recognizes and binds to lock 24 as an antigen. A second binding site 40 recognizes and binds to effector 28, which could be a chelate of yttrium, for example. As noted previously, the chelate could include DOTA or DTPA and $Yt^{90}$, which is a radioactive isotope. The advantage of bifunctional antibody 36 as key 26 is that effector 28 could be administered to the subject at an even later time. In other words, bifunctional antibody 36 could be administered to the subject first. Bifunctional antibody 36 would then attach to the antigen as lock 24. Any free, unbound bifunctional antibody 36 would then be excreted in 24 hours. Finally, effector 28, which could be a chelate of yttrium, could be administered to the subject. The situation could also be reversed, with bifunctional antibody 36 as lock 24. Thus, bifunctional antibody 36 enables greater flexibility for the administration of effector 28.

EXAMPLE 3

Non-protein Antibod/Antigen Combinations

The term "non-protein antibody/antigen combination" is used herein to describe a combination of a non-proteinaceous molecule with antibody-like properties and an antigen, proteinaceous or otherwise. Examples of the non-proteinaceous molecule include, but are not limited to, a carbohydrate macromolecule, a bifuinctional chelator and an oligonucleotide. The carbohydrate macromolecule could be specifically synthesized to be able to bind to the antigen, which could be another carbohydrate. A suitable effector could be selected from those described in any of the Examples or the "Brief Description of the Invention", for example.

Figure 8:
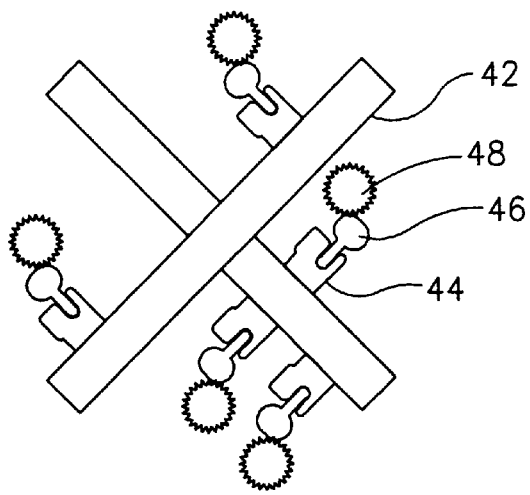
FIG. 8 is a schematic illustration of an exemplary biomedical device system according to the present invention with a carbohydrate macromolecule and an antigen as the lock and key.

FIG. 8 is an illustration of an exemplary biomedical device after administration of a key/effector combination to a subject, in which the key and lock are both non-proteinaceous carbohydrate molecules. Similar to Examples 1 and 2 above, a biomedical device 42 would have a lock 44 attached. Lock 44 could be any type of carbohydrate macromolecule. Lock 44 would specifically bind to a key 46, which would be a complementary carbohydrate macromolecule. Key 46 would have an effector 48 attached, as described in Examples 1 and 2 above.

Figure 9:
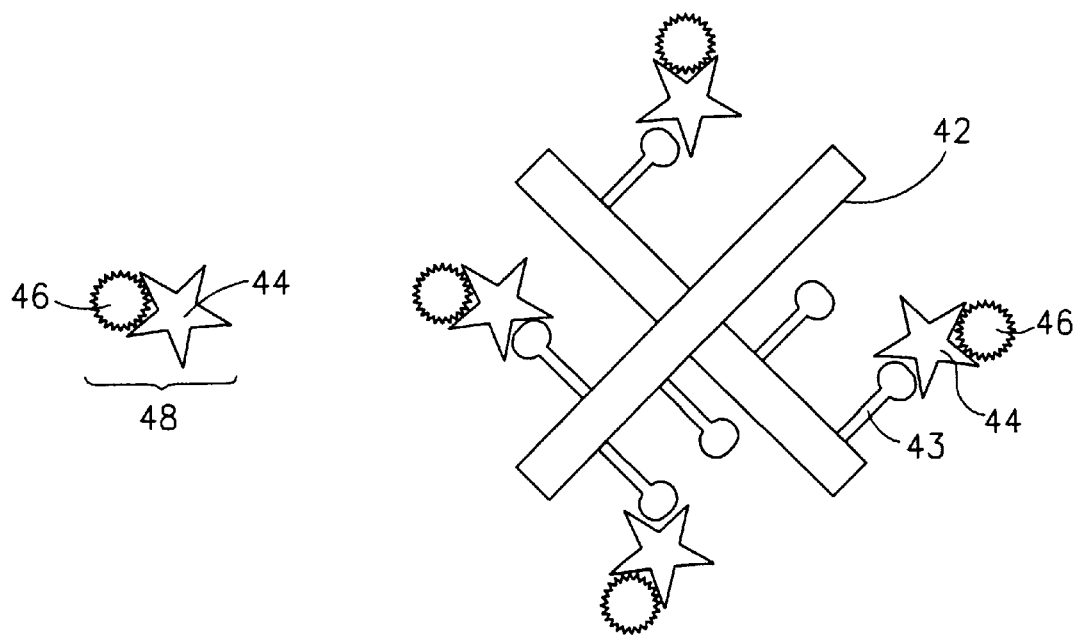
FIG. 9 is a schematic illustration of an exemplary biomedical device system according to the present invention with a bifunctional chelator and an antigen as the lock and key.

As another example, shown in FIG. 9, a bifunctional chelator could be lock 44. Bifunctional chelators are known in the art (Meares et al., *Br. J. Cancer*, 62:21–26, 1990). The bifuinctional chelator would have one functional group which could bind directly to a group on biomedical device 42. For example, if biomedical device 42 featured a metal portion, one functional group of the bifiinctional chelator could bind to the metal portion of biomedical device 42. The other functional group of the bifunctional chelator would be a metal chelator, which could then bind to a radioactive nuclide. The radioactive nuclide would form key 46 and effector 48, since an additional moiety would not be necessary. The radioactive nuclide could be administered to the subject, for example by injection, and would be present in the bloodstream. The radioactive nuclide would be bound by the chelator functional group and concentrated at the location of biomedical device 42.

The advantage of using a non-proteinaceous molecule, such as a carbohydrate molecule, an oligonucleotide or a bifunctional chelator, is that such molecules are less subject to degradation by the body of the subject. Non-proteinaceous molecules can also be administered non-parenterally under some circumstances, and could even be administered orally. These molecules could also be specifically designed to be lock 44 or key 46, without the chemical, synthetic or structural constraints of amino acids or proteins.

Thus, non-proteinaceous molecules could potentially offer more flexibility for the lock and key system of the present invention.

EXAMPLE 4

Mixed Lock and Key system

A mixed lock and key system according to the present invention combines various features of the locks and keys of the previous Examples in order to exploit their desirable properties. Such combinations could include both proteinaceous and non-proteinaceous molecules, or various combinations of each type of molecule. In particular, the mixed lock and key system of the present invention could include an oligonucleotide as at least a component of the key, and an antisense oligonucleotide as at least a component of the lock (Bos, E. S. et al., *Cancer Res.*, 54:3479–86, 1994). The key oligonucleotide would be complementary to the lock oligonucleotide, and would therefore bind specifically to the lock oligonucleotide. Preferably, any type of large macromolecule which could present the oligonucleotide could be attached to the oligonucleotide of the key or of the lock. As part of the lock, such a large macromolecule could enable the oligonucleotide to be attached to the material of the biomedical device while still maintaining spatial separation from that material, for example. As part of the key, such a large macromolecule could providing a binding site or sites for one or more effectors, for example. Thus, although the oligonucleotide could form the lock or key alone, preferably a macromolecule would be attached to the oligonucleotide as part of the lock or key.

For example, the macromolecule could be a protein to which the oligonucleotide was attached, forming a mixed oligonucleotide/proteinaceous complex. The protein could be an immunoglobulin or fragment thereof, avidin or biotin, for example if the binding properties of such a protein were desired. Alternatively, another type of protein without such properties could be used, such as albumin for example.

Alternatively, a non-proteinaceous molecule could be used as the macromolecule. For example, a carbohydrate macromolecule could be used. A bifunctional chelator could also be used to present the oligonucleotide and to bind a radionuclide. Both of these macromolecules would form part of a non-proteinaceous mixed lock and key system according to the present invention.

Figure 10:
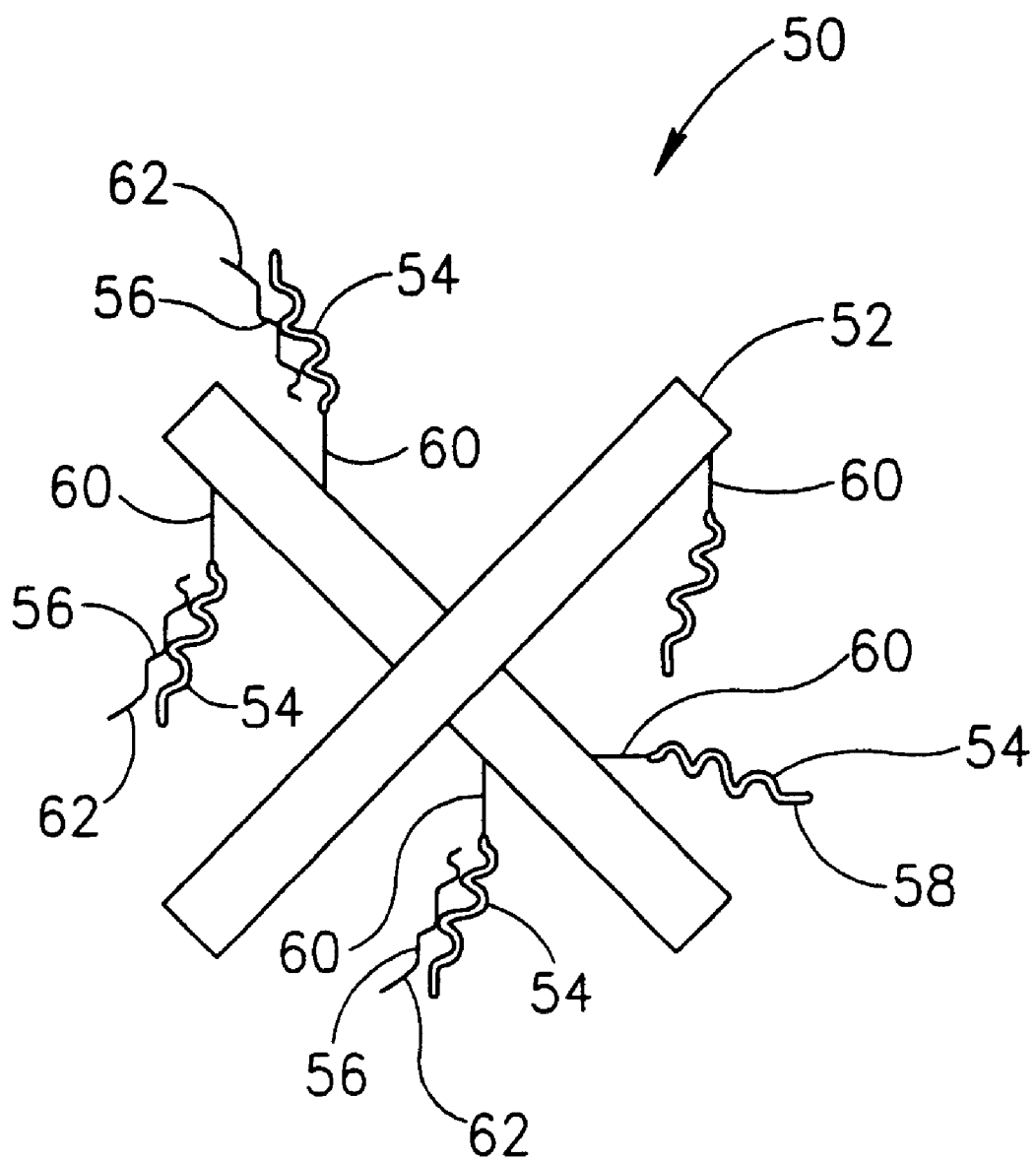
FIG. 10 is a schematic illustration of an exemplary biomedical device system according to the present invention with a mixed lock and key system.

FIG. 10 shows an exemplary mixed lock and key system 50 according to the present invention after administration of the key/effector combination to the subject. Mixed lock and key system 50 includes a biomedical device 52, shown here as a stent for the purposes of illustration, with a lock 54 bound to a key 56. In this example, lock 54 includes a sense lock oligonucleotide 58 attached to a suitable spacer 60. Spacer 60 could be an organic polymer, a carbohydrate macromolecule or a peptide, for example. Key 56 includes an antisense key oligonucleotide 62. Although not shown, key oligonucleotide 62 could be attached to any suitable macromolecule as described previously, either directly or through a suitable spacer such as an organic polymer, a carbohydrate macromolecule or a peptide, for example. Furthermore, key 56 could also be attached to a suitable effector (not shown) substantially as described in any of the Examples or the "Brief Description of the Invention".

EXAMPLE 5

Methods of Production

The biomedical device systems of the present invention can be manufactured in a number of different ways. First, a biomedical device would be manufactured according to methods well known in the prior art. Next, a lock could be attached to the biomedical device. The next step would depend upon whether the system was being manufactured in vivo or ex vivo. For ex vivo production, the key would then be added and allowed to attach to the lock. The completed biomedical device system would then be placed within the subject. For in vivo production, the biomedical device with the lock attached would be placed within the subject. The key would be administered to the subject and allowed to attach to the lock, thereby completing the biomedical device system.

Several examples are given herein for the manufacture of stents as illustrative biomedical devices, it being understood that this is for the purposes of illustration only and is not meant to be limiting in any way. Two examples are given for ex vivo manufacture of the biomedical device system, and one example is given for in vivo manufacture of the biomedical device system.

Method 1: Ex vivo Manufacture of a Radioactive Stent

First, a stent is manufactured according to regular manufacturing practices for a biomedical device. At least a portion of the stent, such as the inner surface, preferably is made from a derivatizable polymer. Alternatively and preferably, the inner surface could be made from metal, and then coated with a derivatizable polymer. The derivatizable polymer preferably features functional groups which can form covalent cross-link bonds with a lock moiety, such as a protein, upon exposure to a catalyst such as an ultraviolet light source. Alternatively and preferably, a non-covalent bond could be formed between the lock and the material of the stent. Also alternatively and preferably, the lock moiety could form covalent bonds with a metal portion of the stent.

Next, the derivatizable polymer is derivatized by attaching a lock, such as an antigen, to the polymer. The attachment occurs by incubating the antigen or other moiety with the polymer of the stent under suitable conditions, and then exposing the stent to an activator if necessary. For example, to form a covalent bond between the lock and the derivatizable polymer, the activator could be ultraviolet light.

In the next step, the key and effector combination is incubated with the stent under suitable conditions, so that the key and lock bind. For example, if the lock was an antigen, the key could be an antibody with a radioactive isotope as the effector. The antibody would bind to the antigen, so that the radioactive isotope was connected to the stent. The stent would thus become radioactive, and would now be ready for implantation within the subject.

In a variation on this method, the lock, key and effector could be one unit which would be bound directly to the stent. For example, the antibody with the radioactive isotope could be bound directly to the polymer of the stent, to form a radioactive stent.

In another variation, the antigen would again be bound as the lock to the stent. Next, a bifunctional antibody would be allowed to bind to the lock as the key. One binding site of the bifunctional antibody would bind to the antigen, while the other binding site would bind to the effector. The effector could be a chelated isotope, such as the combination of DOTA or DTPA and yttrium or cobalt described previously. Once the chelated radioisotope was bound, the stent would again become radioactive and would be ready for implantation within the subject.

Method 2: Ex vivo Manufacture of a Coated Stent

As noted previously, coating the inner surface of a stent with endothelial cells has been proposed as a way to inhibit the formation of thrombi or atheriosclerosis around the stent. Endothelial cells normally line the blood vessel, so a stent which also had these cells growing in the interior would be able to more closely mimic the natural state of the blood vessel. Unfortunately, no method has yet been proposed for manufacturing such endothelial-cell coated stents outside of the research laboratory. The present invention is uniquely able to provide such stents, in which the endothelial cell is either a key according to the present invention, or else is directly attached to the stent surface.

A stent is manufactured and prepared as described for Method 1 above. The lock could be an antibody specific for some portion of endothelial cells so that the antibody binds specifically to these cells. Next, endothelial cells are incubated with the stent under suitable conditions, so that the antibody binds to the endothelial cells. The inner surface of the stent is coated with endothelial cells. The stent is now ready to be implanted within the body of the subject.

Alternatively and preferably, an antigen could be attached to the stent as described previously. An antibody with an attached endothelial cell could then be incubated with the stent, so that the antibody binds to the antigen. The stent is now coated with endothelial cells. The antibody could be a bifunctional antibody, so that the attachment of the antibody to the endothelial cell is noncovalent. Alternatively and preferably, the antibody could be covalently attached to a protein or other moiety on the surface of the endothelial cell. Of course, fragments of immunoglobulins, other types of proteins or non-protein macromolecules could be used in place of the antibody for attachment of the endothelial cell to the stent.

One example of a particularly preferred system for attaching the endothelial cells to the stent would involve attaching an adhesion molecule to the stent, and then incubating the stent with endothelial cells ex vivo. These adhesion molecules, such as cadherin, are normally located on endothelial cells, and cause these cells to adhere to one another. By attaching these adhesion molecules to the stent, the endothelial cells would thus adhere to the stent. Similarly, antibodies which bind selectively to these adhesion molecules could also be attached to the stent, and would then cause the endothelial cells to adhere to the stent.

In addition, the biomedical device system could optionally be completed in vivo, by administering an endothelial cell, alone or in combination with an antibody or other suitable macromolecule, to the subject. For example, the endothelial cell/antibody combination could be injected locally into a vessel of the subject after implantation of the stent to which an antigen was attached. The vessel may be occluded transiently with balloon catheters to prevent displacement of endothelial cells from blood flowing through the vessel. The remaining unattached endothelial cells may be removed prior to terminating the procedure in order to prevent embolization and undesired medical complications.

Method 3: In vivo Production of a Radioactive or Coated Stent

As described in Method 1 above, a lock is attached to a stent. Next, the stent is inserted into a blood vessel of a subject. Next, a key and effector, such as an antibody with a radioactive isotope attached, or an antibody attached to an endothelial cell, could be administered to the subject. The key would then bind to the lock, thereby specifically delivering the effector to the area immediately surrounding the biomedical device. For example, the radioactive isotope attached to the antibody would localize to the stent, thereby specifically treating the tissue surrounding the stent with radioactivity. Alternatively, the endothelial cells would coat the stent to form a coated stent in vivo as described above, which would specifically treat the surrounding tissue with endothelial cell products such as nitric oxide.

EXAMPLE 6

Exemplary Effectors

The term "effector" includes any molecule, combination of molecules or even a complete cell, which has a therapeutic effect. For example, the effector could be a radioactive isotope, a drug, a hormone, a growth factor, a cytokine, a T-cell or a toxin. The effector could be selected in order to inhibit tissue growth, for example to treat or prevent restenosis. Another example of an effector could be an endothelial cell, particularly for coating the interior surface of a stent in order to prevent formation of thrombi. In some circumstances, the effector and the key could be the same moiety. For example, a chelate of a metal could specifically bind to a lock, such as an antibody, on a biomedical device. The chelate could include DOTA or DTPA and yttrium, for example. Yttrium is an example of a potentially radioactive isotope which is used for the inhibition of tissue growth.

Another type of effector would be a bi-component effector with an enzyme attached to the antibody. The enzyme would activate a prodrug by chemically altering the prodrug. Preferably, the prodrug would have little or substantially no effect on the subject. However, the activated drug would have a desired effect or effects for treatment. For example, the activated drug could be a cytotoxic drug for the inhibition of restenosis. Thus, many different types of effectors are possible and could be selected by one of ordinary skill in the art.

Radionuclides as Effectors

Localized radioimmunotherapy has been particularly extensively studied for the treatment of cancer. For example, antibodies with radionuclides such as yttrium 90 ($^{90}$Y), iodine 131 ($^{131}$I) and copper 67 ($^{67}$Cu) have been used to successfully treat B-cell non-Hodgkin's lymphoma (Wilder, R. B. et al., *J. Clin. Oncol.*, 14:1383–1400, 1996). However, relatively low levels of localization of radionuclide-labelled antibodies to solid tumors have been shown to be effective for treatment. For example, 0.1% to 10% specific binding of such antibodies to solid tumors has still resulted in effective therapy. Thus, low levels of localization of antibodies to biomedical devices of the present invention would presumably be sufficient for effective treatment.

The selection of a particular radionuclide depends upon the intended therapy. For example, the maximal tumor dose rates are higher for antibodies with yttrium 90 and copper 67 attached (about 0.40 Gy/h) than for antibodies with iodine 131 attached (about 0.10 Gy/h) (Wilder, R. B. et al., *J. Clin. Oncol.*, 14:1383–1400, 1996). However, dose rates as low as 0.02 to 0.03 Gy/h have been estimated as the minimum dose to halt proliferation of malignant cells in vivo (Wilder, R. B. et al., *J. Clin. Oncol.*, 14:1383–1400, 1996). Since certain embodiments of the biomedical device system of the present invention are intended to inhibit or to prevent tissue growth in the surrounding area, presumably this therapeutically effective dosage would also apply to these embodiments of the system of the present invention. Certainly the teachings of the prior art with regard to the treatment of cancer with radionuclide-labelled antibodies could be applied to these embodiments of the biomedical device system of the present invention. Thus, the use of radionuclide-labelled antibodies for the treatment of cancer is well known in the art.

Chelates as Effectors

Radionuclides are often used as part of a chelated complex. For example, yttrium, cobalt and indium can be chelated with a chelator such as DTPA (1,4,7-triazaheptane-N,N',N"-pentaacetic acid), DOTA (1,4,7,10-tetraazacyclododecane-N,N',N",N'''-tetraaceticacid) or with derivatives thereof, such as nitrobenzyl-DOTA (2-p-nitrobenzyl-1,4,7,10-tetraazacyclododecane-N,N',N",N'''-tetraacetic acid). These chelated radionuclides can then be specifically bound by antibodies against the chelator to form the key/effector complex of the present invention. Antibodies with high specific binding to such chelators are known in the art (Kranenborg, M. H. G. C. et al., *Can. Res. Supp.*, 55:5864–5867, 1995; Meares, C. F., et al., *Br. J. Cancer*, 62:21–26, 1990). Thus, a complex of a chelator with a radionuclide could be used as an effector for the biomedical device system of the present invention.

In addition, a bifunctional chelating agent which features a strong metal chelating group at one end and a reactive functional group capable of binding to proteins at the other end. An example of such an agent is a macrocylic bifunctional molecule such as a conjugate of nitrobenzyl-DOTA and an immunoglobulin or a fragment thereof. The biomedical device would feature an attached antigen as the lock. The key and effector combination would be the macrocyclic bifunctional chelating agent, which would have the immunoglobulin or fragment thereof as the key, and the chelator and radioactive isotope as the effector. In another variation the biomedical device would feature the immunoglobulin or fragment thereof as the lock, and the key would be a bifunctional chelating agent. This bifunctional agent would have a functional group capable of binding to the immunoglobulin or fragment thereof, as well as a chelator group for chelating the radionuclide, which would be the effector.

Toxins as Effectors

Many different types of toxins have been used for localized therapy, particularly for cancer. Hereinafter, the term "toxin" includes any cytotoxic moiety. Examples of toxins include, but are not limited to, plant toxins such as ricin, modeccin, viscumin, pokeweed anti-viral protein, saporin, gelonin, momoridin, trichosanthin, barley toxin and abrin, bacterial toxins such as diptheria toxin and Pseudomonas endotoxin, fungal toxins such as alpha-sarcin and restrictocin, and synthetic toxins. Plant, bacterial and fungal toxins often have their effect through inhibition of protein synthesis. For example, diptheria toxin and Pseudomonas endotoxin both inactivate elongation factor 2, while ricin and abrin inactivate the 28S ribosomal subunit (Thrush, G. R. et al., *Ann. Rev. Immunol.*, 14:49–71, 1996). Other toxins may inhibit other activities of the cell, such as DNA synthesis or mitochondrial activities. When attached to a targeting moiety such as an antibody, these toxins have been used in vitro to remove tumor cells for autologous bone marrow transplantation, and for in vivo treatment of patients with cancer, autoimmune disease and HIV infection (Thrush, G. R. et al., *Ann. Rev. Immunol.*, 14:49–71, 1996).

With regard to the present invention, these toxins are particularly contemplated as effectors for the inhibition of tissue growth in the area immediately surrounding the biomedical device in certain embodiments of the biomedical device system of the present invention. For example, these toxins could be used to prevent restenosis in a blood vessel after a stent had been implanted. The teachings of the use of these toxins for localized therapy for cancer and other diseases could also be incorporated for such embodiments of the present invention. One advantage of the system of the present invention over these prior art methods is that the antibody and antigen, or other lock and key system, could be specifically designed and tested in vitro, before a biomedical device coated with the selected lock was implanted in vivo.

Thus, the system of the present invention provides potentially even greater specificity for targeting such toxins to the tissue to be treated.

Endothelial Cells as Effectors

Most of the previous examples of effectors were drawn toward effectors which inhibited or prevented tissue growth by their effects on cell growth and proliferation. However, endothelial cells are contemplated as an example of an effector which is itself a cell. Endothelial cells would be particularly effective as an effector for coating stents in order to prevent or reduce the occurrence of the formation of thrombi, as described in Example 4 previously. Endothelialization of stents, in which endothelial tissue grows into and surrounds stents, is already well known in the art (Van Belle, E. et al., Circulation, 95:438–448, 1997). The use of endothelial cells for coating stents according to the present invention would be markedly different. As contemplated herein, the endothelial cells would be attached to an antibody, which would then bind to an antigen attached to the stent, for example. Thus, the rate of endothelialization could be completely controlled by such coating of stents with endothelial cells, according to one embodiment of the biomedical device system of the present invention.

It will be appreciated that the above descriptions are intended only to serve as examples, and that many other embodiments are possible within the spirit and the scope of the present invention.

What is claimed is:

1. A method of substantially inhibiting restenosis in a blood vessel of a subject, comprising the steps of:
   (a) inserting a stent into the blood vessel of the subject, said stent having an antigen attached; and
   (b) administering a first antibody to the subject, said first antibody being capable of binding to said antigen and said first antibody having a label attached wherein said label is capable of inhibiting restenosis and wherein said label is a radioactive source.

2. The method of claim 1, further comprising the steps of:
   (c) administering a seconid antibody to the subject, said second antibody being capable of binding to said antigen and said second antibody being without said label attached; and
   (d) displacing said first antibody from said antigen with said second antibody.

3. The method of claim 2, wherein said radioactive source is selected from the group consisting of yttrium 90 ($^{90}$Y), lutetium 177 ($^{177}$Lu), rhenium 186 ($^{186}$Re), rhenium 188 ($^{188}$Re), bismuth 212 ($^{212}$Bi), astatine 211 ($^{211}$At), iodine 131 ($^{131}$I), iodine 125 ($^{125}$I) and copper 67 ($^{67}$Cu).

4. A method for manufacturing a biomedical device assembly, the method comprising the steps of:
   (a) providing a biomedical device;
   (b) attaching a lock to said biomedical device;
   (c) attaching an effector to a key to form an attached effector, wherein said effector is a radioactive isotope; and
   (d) incubating said lock and said key, such that said lock and said key interact to form the biomedical device assembly.

5. The method of claim 4, wherein said lock is at least a portion of an adhesion molecule.

6. The method of claim 5, wherein the step of attaching said lock to said biomedical device is performed ex vivo, and the step of incubating said lock and said key to form the biomedical device assembly is performed by first placing said biomedical device with said lock in a subject, and then administering said key with said attached effector to said subject, such that the biomedical device assembly is formed by an interaction of said key and said lock in said subject.

7. The method of claim 5, wherein the step of attaching said lock to said biomedical device is performed ex vivo, and the step of incubating said lock and said key to form the biomedical device assembly is performed ex vivo.

8. The method of claim 4, wherein said lock is an antibody binding specifically to at least a portion of an adhesion molecule, said portion being sufficient for binding said endothelial cell.

9. The method of claim 8, wherein the step of attaching said lock to said biomedical device is performed ex vivo, and the step of incubating said lock and said key to form the biomedical device assembly is performed by first placing said biomedical device with said lock in a subject, and then administering said key with said attached effector to said subject, such that the biomedical device assembly is formed by an interaction of said key and said lock in said subject.

10. The method of claim 8, wherein the step of attaching said lock to said biomedical device is performed ex vivo, and the step of incubating said lock and said key to form the biomedical device assembly is performed ex vivo.

11. The method of claim 4, wherein said radioactive source is selected from the group consisting of yttrium 90 ($^{90}$Y), lutetium 177 ($^{177}$Lu), thenium 186 ($^{186}$Re), rhenium 188 ($^{188}$Re), bismuth 212 ($^{212}$Bi), astatine 211 ($^{211}$At), iodine 131 ($^{131}$I), iodine 125 ($^{125}$I) and copper 67 ($^{67}$Cu).

12. The method of claim 4, wherein said key is an antibody for specifically binding to said lock.

* * * * *